(12) United States Patent
Cassell (10) Patent No.: US 7,179,264 B2
(45) Date of Patent: Feb. 20, 2007

(54) CEMENTED PROSTHETIC KIT (75) Inventor: Dennis R. Cassell, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/231,413

(22) Filed: Aug. 28, 2002

(65) Prior Publication Data

US 2004/0044347 A1 Mar. 4, 2004

(51) Int. Cl.
*A61F 2/36* (2006.01)

(52) U.S. Cl. ...................... 606/92; 623/22.11

(58) Field of Classification Search .................. 606/92, 606/80; 623/22.11, 22.12, 16.11, 18.11
See application file for complete search history.

(56) References Cited

U.S. PATENT DOCUMENTS

| | | | | |
|---|---|---|---|---|
| 3,869,731 A * | 3/1975 | Waugh et al. | ........... | 623/20.21 |
| 4,302,855 A | 12/1981 | Swanson | | |
| 4,457,028 A * | 7/1984 | Draenert | ................. | 623/23.59 |
| 4,849,223 A * | 7/1989 | Pratt et al. | ................. | 424/409 |
| 5,045,054 A * | 9/1991 | Hood et al. | .................... | 604/22 |
| 5,171,275 A | 12/1992 | Ling | | |
| 5,370,706 A | 12/1994 | Bolesky et al. | | |
| 5,470,336 A * | 11/1995 | Ling et al. | ................... | 606/105 |
| 5,593,452 A * | 1/1997 | Higham et al. | .......... | 623/23.38 |
| 5,766,178 A * | 6/1998 | Michielli et al. | ............. | 606/95 |
| 5,776,200 A | 7/1998 | Johnson et al. | | |
| 5,871,549 A | 2/1999 | Jayashankar et al. | | |
| 5,972,034 A * | 10/1999 | Hofmann et al. | ........ | 623/23.48 |
| 6,017,349 A * | 1/2000 | Heller et al. | .................. | 606/92 |
| 6,158,437 A * | 12/2000 | Vagley | ........................ | 128/898 |
| 6,165,177 A | 12/2000 | Wilson et al. | | |
| 6,264,699 B1 | 7/2001 | Noiles et al. | | |
| 6,299,642 B1 * | 10/2001 | Chan | ......................... | 623/16.11 |
| 6,309,395 B1 | 10/2001 | Smith et al. | | |
| 6,800,245 B1 * | 10/2004 | Erbe et al. | ...................... | 422/1 |
| 2003/0023250 A1 * | 1/2003 | Watschke et al. | ............ | 606/148 |
| 2004/0171924 A1 * | 9/2004 | Mire et al. | ................... | 600/407 |

FOREIGN PATENT DOCUMENTS

| | | |
|---|---|---|
| FR | 2 710 257 | 3/1995 |
| GB | 2180815 A * | 4/1987 |
| WO | WO 00 45723 | 8/2000 |

* cited by examiner

*Primary Examiner*—Eduardo C. Robert
*Assistant Examiner*—David Comstock
(74) *Attorney, Agent, or Firm*—Maginot, Moore & Beck (57) ABSTRACT A kit (10) for use in implanting a stem (12) into a long bone (36) for use in joint arthroplasty is provided. The kit (10) includes a stem (12) for implantation into the long bone (36), a cement restrictor (16), and a quantity of bone cement (20).

19 Claims, 8 Drawing Sheets

CEMENTED PROSTHETIC KIT

TECHNICAL FIELD OF THE INVENTION

The present invention relates generally to the field of orthopaedics, and more particularly, to an implant for use in arthroplasty.

BACKGROUND OF THE INVENTION

The invention relates to joint prostheses. More particularly, the invention is directed to cemented stems for engagement with long bones adjacent a prosthetic joint, bone cement and related devices.

Joint replacement surgery is a quite common remedy for osteoarthritis and rheumatoid arthritis. It enables many individuals to function normally when otherwise it would not be possible to do so. Artificial joints are usually comprised of metallic, ceramic and or plastic components that are fixed to existing bone. Such joint prostheses include components for artificial replacement joints for the anatomical joints of elbows, hips, knees, and shoulders. An important consideration in the design and manufacture of virtually any implantable bone prostheses is that the bone prostheses has adequate fixation when implanted within the body.

Early designs of implantable prosthetic joints have relied upon the use of cements such as polymethylmethacrylate (PMMA) to anchor the implant. The use of such cements can have some advantages, such as providing a fixation that does not develop free play or does not lead to erosion of adjoining faces post-operatively. Maintaining a load or force at the bone/cement interface assists in providing for good fixation and to prevent motion. Later designs of implantable articles include implant surfaces that have contours which permit bony in-growth within the implant and which are press-fitted into the bone cavity. The use of the press-fitted stems has been found to be more suitable where the condition of the bone is healthier. For those patients in which osteoarthritis and rheumatoid arthritis have progressed to the point that the bones are highly diseased, the use of a cemented prosthesis is often advised.

When implanting an orthopedic joint implant into a long bone, the orthopedic implant component includes a stem which is fitted into the long bone. The long bone is typically resected and tools in the form of, for example a combination of drills, reamers, and broaches are utilized to prepare the cavity in the long bone. The cavity in the long bone is made larger than the stem of the implant and a layer of cement is positioned between the stem and the cavity of the long bone. Such long bones include the femur, the tibia, the humerus and the ulna for example.

The preparation and procedure for total joint implants, particularly for inserting and positioning stems within a long bone, require additional tools in addition to the drills, reamers, and broaches required for preparing the bone cavity. These tools are necessary to assure a clean, uncontaminated cavity for the filling of the cavity with the bone cement and the prosthetic stem. Such additional tools may include a stem centralizer to centralize the distal portion of the prosthetic stem and cement restrictors which are positioned distally in the stem for isolating the cement to a position proximal of the distal portion of the stem and for preventing the migration of other human tissues distally of the cement restrictor.

Additional equipment desired in a cement prosthetic stem arthroplasty procedure include a femoral pressurizor to assist in pressurizing in this cement. Pressurizing of this cement is advisable to assure that a complete uniform mantle of cement surrounds the stem to support and secure the stem to the bone cavity.

Further to remove the debris created in the tip of the bone cavity during the drilling, reaming, and/or broaching, additional tools are desirable to remove these bone fragments. Such tools include curettes used to remove excess bone cement from the bone cavity. Femoral sponges are also utilized to remove blood and bone debris from the bone cavity. In addition, femoral brushes may be utilized to clean the bone fragments and other debris from the bone cavity.

While cemented stems are generally secured by PMMA, significant differences in PMMA are available. Some PMMA bone cements have very slow curing time while others have quicker curing times. Further, the PMMA cement may include additional compounds to either reduce infection or reduce the pain or such compounds may be anticipated in the future. Further cements may be designed to be more compatible with a particular stem design. It may thus be desirable therefore, to implant a particular prosthetic stem with a particular PMMA cement design for that stem.

Total joint arthroplasty is typically performed in an operating room in a hospital. Typically the operating room is used for any of a wide variety of surgical procedures. Total joint arthroplasty, as with many surgical procedures, requires a large number of instruments as well as the required implants for the surgery. The instruments for the total joint arthroplasty procedures as well as instruments and other equipment necessary for the wide variety procedures for the operating room within the hospital must be maintained in inventory or specifically ordered for the procedure. The need for this vast array of instruments and equipment creates a inventory control and scheduling complexity for the hospital. It is, however, important that the proper instruments and implants are available to the surgeon for a procedure.

While a total joint arthroplasty may be performed if the broach and reamer is available for the preparation of the stem as well as the PMMA cement and the implant, problems can occur when all the necessary cement implant products are not available. For example, if a cement restrictor is not available, it may be difficult for the surgeon to achieve a sufficient pressurization of cement in the femoral canal. The lack of sufficient pressurization in the canal may lead to potential voids within the cement mantle and may result in less than optimal result in the total joint arthroplasty. Similarly, the lack of cement restrictors or centralizers may result in a less than ideal cement mantle for the total joint arthroplasty.

While the availability of all the items necessary for a successful total joint arthroplasty is somewhat difficult to accomplish, the problem is exacerbated for total joint arthroplasty procedures that are not planned. Total joint arthroplasty procedures may be performed as a result of trauma. Such procedures may use what is known as a fracture stem which is implanted in the event of a trauma to the hip. Such fracture stems are often implanted after hours when the trauma occurs. The after hours on call staff may be as not as familiar with the hospital inventories as the regular staff and the after hour staff may have difficulty collecting all the items necessary to perform this surgery.

The present invention is directed to solve at least some of the aforementioned problems.

SUMMARY OF THE INVENTION

According to the present invention, a single package is provided that includes a prosthetic stem as well as a cement restrictor and a quantity of bone cement sufficient for the procedure. The kit may also include other disposable cement preparation tools as well as a cement centralizer.

The present invention may include an outer package that contains several inner packages containing, for example, a hip stem implant, a restrictor, a dose of bone cement sized and selected for one anthroscopic procedure, one disposable preparation kit, universal cement restrictors, and a cement restrictor inserter. The package may be provided sterile through the end user.

The package of the present invention solves the problem of not having all the required products available to properly implant a cemented stem. By packaging all the components together, the components are readily available when required for a surgical procedure. Packaging these products together helps prevent problems that can occur when all the necessary products are not available. The package of the present invention represents a solution that is optimal in that it removes as many variables as possible in the packaging and inventory.

The present invention may include a combined single outer package for containing all the elements while providing for individual packaging of each element within the single outer package.

According to one embodiment of the present invention, there is provided a kit for use in implanting a stem into a long bone for use in joint arthroplasty is provided. The kit includes a stem for implantation into the long bone, a cement restrictor, and a quantity of bone cement.

According to another embodiment of the present invention there is provided a kit for use in implanting a stem into a long bone for use in joint arthroplasty is provided. The kit includes a stem for implantation into the long bone, a cement restrictor, a stem centralizer, a quantity of bone cement, and a monomer for activating the bone cement.

According to yet another embodiment of the present invention there is provided a kit for use in implanting a stem into a long bone for use in joint arthroplasty is provided. The kit includes a stem for implantation into the long bone, a first cement restrictor, a second cement restrictor, a cement restrictor inserter, a cement curette, a stem centralizer, a quantity of bone cement, and a monomer for activating the bone cement.

The technical advantages of the present invention include improved convenience to the operating room and hospital staff. For example, according to one aspect of the present invention, a kit for use in implanting a stem into a long bone is provided which includes a cement restrictor, a cement centralizer, and quantity of bone cement, a stem, and a monomer for activating the bone cement. This kit provides for convenience by freeing the hospital staff from individually determining, selecting and obtaining the various components separately.

Another technically advantage of the present invention includes the potential safety improvement by insuring that all necessary products and cement accessories are readily available. For example, according to another aspect of the present invention, a kit for use in implanting a stem into a long bone for use in joint arthroplasty is provided which includes a stem, a cement restrictor, and a quantity of bone cement Thus, the present invention provides for a kit which insures that all necessary cement products and cement accessories are readily available for the operating staff.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
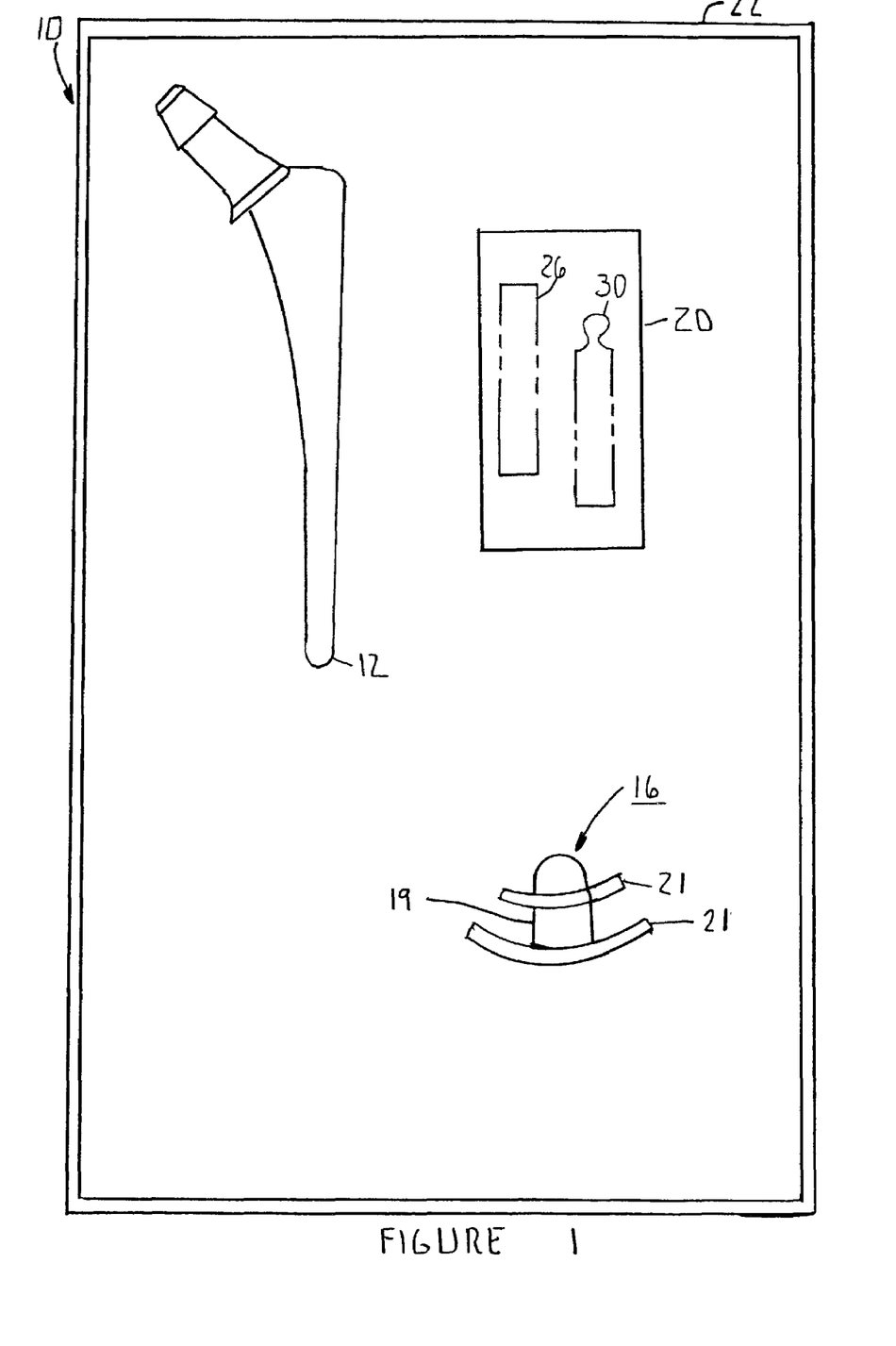
FIG. 1 is a top view of a kit for use in implanting a stem into a long bone for use in joint arthroplasty including a stem, a cement restrictor and a quantity of bone cement in accordance with an embodiment of the present invention.

According to the present invention and referring now to FIG. 1, a kit 10 is provided. The kit 10 is for use in joint arthroplasty in a long bone. The kit 10 includes a stem 12 for implantation in a long bone. While the stem 12 as shown in FIG. 1 is a femoral hip stem, the invention may be practiced where the stem is a femoral knee stem, a tibia knee stem, a humeral shoulder stem, or any other long bone stem. The kit 10 further includes a quantity of bone cement 20. Preferably and as shown in FIG. 1, the stem 12, cement restrictor 16 and bone cement 20 are commonly packaged in outer package 22. The outer package 22 is utilized to keep all components of the kit together for use in the total joint arthroplasty. The outer package 22 further may serve as a means for maintaining the sterilization of at least one of the stem 12, the cement restrictor 16 and the bone cement 20.

The outer package 22 may be made of, for example, a moldable plastic or paper. When made of paper, the outer package 22 may include a plastic overwrapping. It should be appreciated that the stem 12, cement restrictor 16 and bone cement 20 may be separately sterilized or be sterilized together in the outer package 22. Any sufficient sterilizing technique may be utilized including any combination of heat, inert gas, or irradiation. For example, the kit 10 may be sterilized using gas plasma sterilization or gamma irradiation.

The cement restrictor 16 may have any suitable shape and be made of any suitable durable material that is compatible with the human body and sterilizable. For example, the cement restrictor 16 may be made of PMMA or a plastic, for example, ultra high molecular weight polyethylene. The cement restrictor 16 may have a shape capable of restricting the progress of the cement distally within the bone canal. For example, the cement restrictor 16 may include a body 19 with circumferential fins 21 extending outwardly from the body 19.

The bone cement 20 may be any suitable bone cement and may for example be PMMA. Typically, PMMA bone cement 20 includes a powder 26 which is activated by a liquid monomer 30. The bone cement 20 may be a fast acting bone cement or a more slowly acting bone cement. Further the bone cement 20 may include additional additives to perform particular functions such as antiseptic or as analgesic functions.

Figure 2:
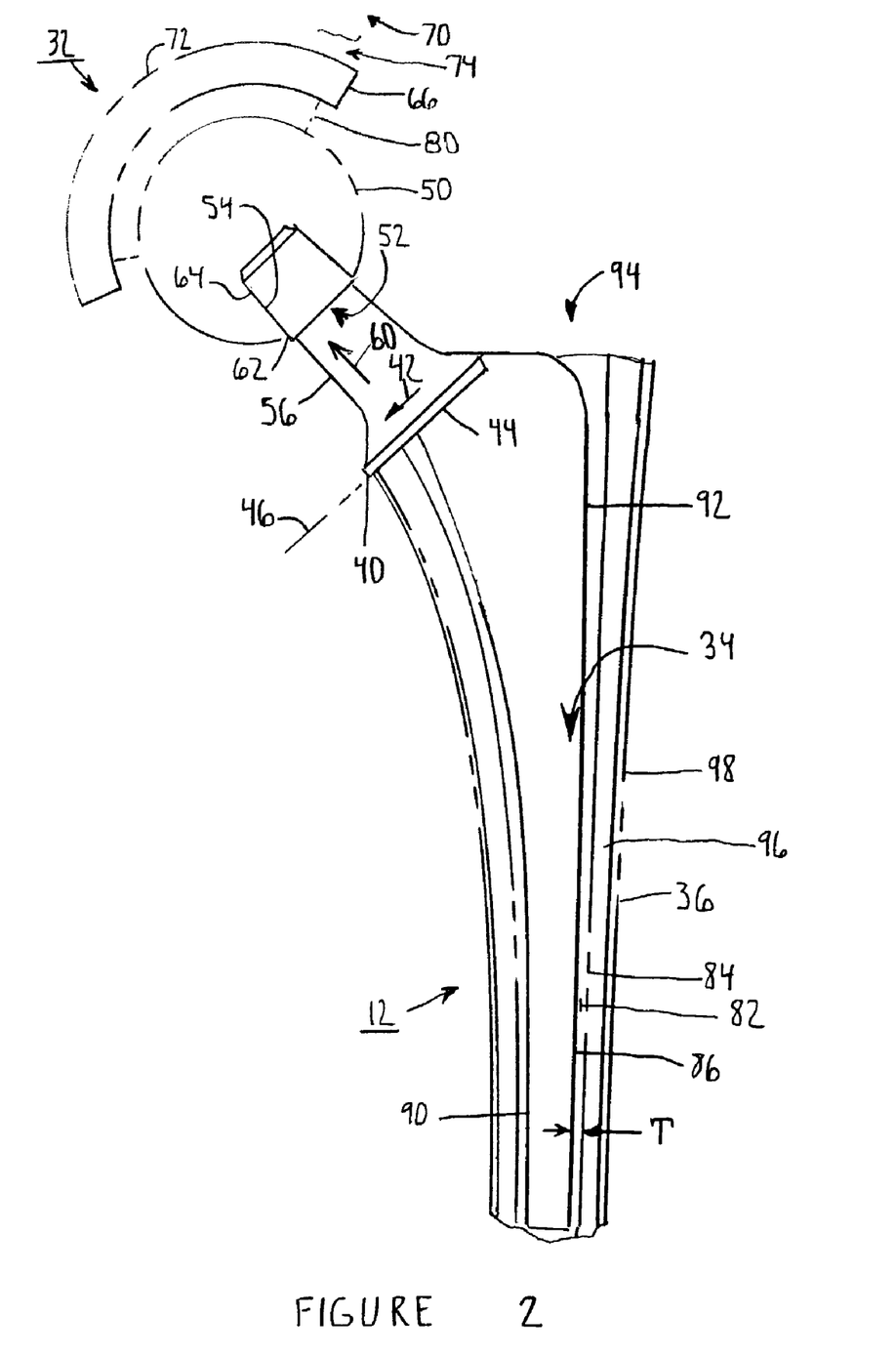
FIG. 2 is a medial lateral plan view of the stem of FIG. 1.
Figure 3:
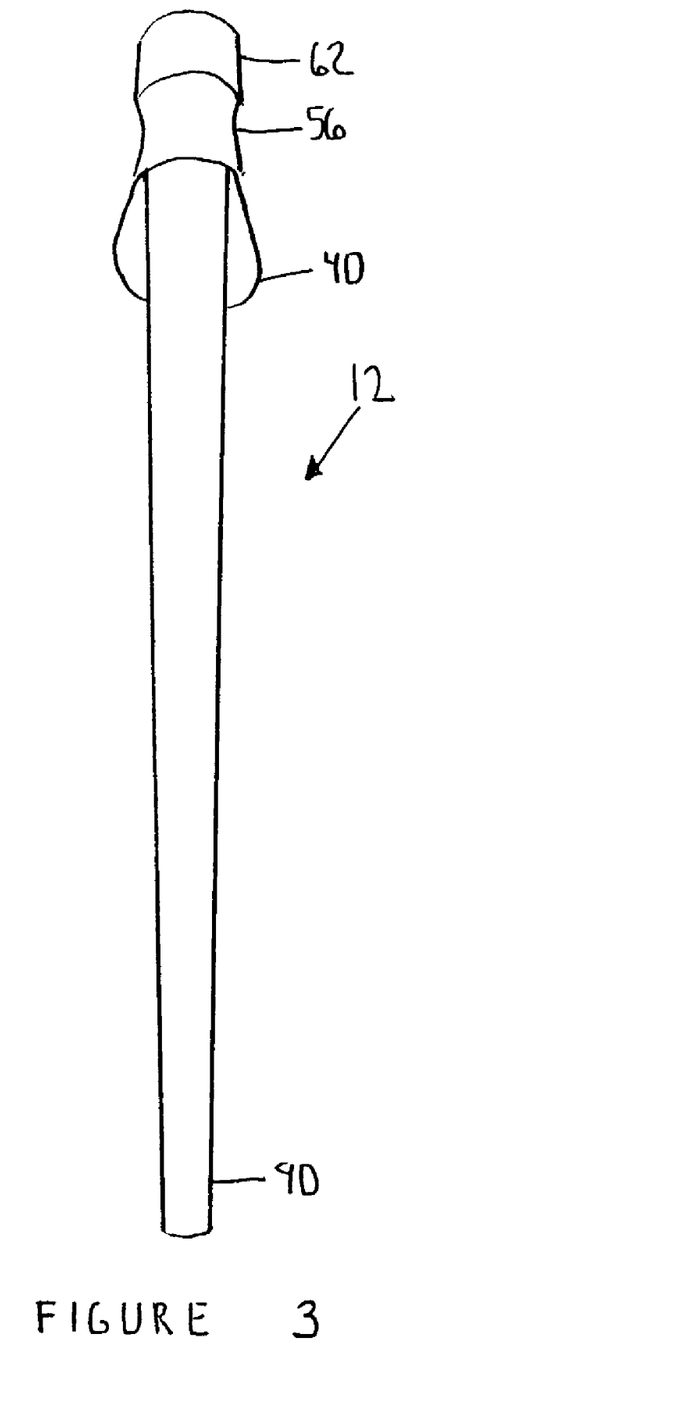
FIG. 3 is a anterior posterior plan view of the stem of FIG. 1.

Referring now to FIGS. 2 and 3, the stem 12 is shown in greater detail. The stem 12 as shown in FIG. 2, is a part of a hip prosthesis 32. As shown in FIG. 2, the stem 12 is suitable for implantation at least partially within medullarally canal 34 of long bone or femur 36.

The prosthesis 32 may includes a collar 40 for positioning during surgery the prosthesis 32 within the long bone 36. The collar 40 is operably associated with the stem 12 and extends outwardly in the direction of arrow 42 from the stem 12. The collar 40 may include a collar face 44 which is positioned against resected face 46 of the long bone 36. The collar 40 thus serves to support the prosthesis 32 against the long bone 36 and to provide a reference for proper positioning of the prosthesis 32 within the medullary canal 34 of long bone 36.

Alternatively, the prosthesis 32 may be made without a collar. One such prosthesis is the "C-Stem" hip prosthesis sold by DePuy Orthopaedics, Inc.

Preferably, as is shown in FIG. 2, the prosthesis 32 further includes a head 50 which operably associated with the stem 12. The head 50 may be operably associated with the stem in any suitable manner. For example, the head 50 may include a cono-frustrical recess 52 forming an internal tapered surface 54.

As shown in FIGS. 2 and 3, the stem 12 may include a neck 56 extending proximately in the direction of arrow 60 from the collar 40. The neck 56 may include an externally tapered portion 62 having an external surface 64. The external surface 64 of the tapered portion 62 of the neck 56 is matingly fitted to the internal surface 54 of the head 50.

The prosthesis 32 may further include a cup 66 for rotatable engagement with the head 60. The cup 66 may be secured to hip bone 70 in any suitable fashion. For example, the cup 66 may include a hemi spherically outer surface 72 which matingly fits with acetabulum 74 of the hip bone 70. The outer surface 72 of the cup 66 may include openings (not shown) to which fasteners (not shown) are fitted for securement to the acetabulum 74 or may include a threaded periphery (not shown) for engagement with the acetabulum 74. Alternatively, the outer surface 72 may include a porous coating to assist bone-ingrowth.

The cup 66 may be in pivotal engagement with the head 50 in any suitable fashion. For example, the head 50 and the cup 66 may have mating surfaces for metal to metal contact with each other or, as shown in FIG. 2, a liner 80 may be positioned between the cup 66 and the head 50.

The liner 80 may be made of any durable material and may be made of a nonmetallic material, for example, a plastic or ceramic. For example, the liner 80 may be made of a ultra high molecular weight polyethylene. One particular ultra high molecular weight polyethylene that is well suited for this application is sold by DePuy as Marathon® and is generally described in U.S. Pat. Nos. 6,017,975 and 6,228,900 which are hereby incorporated by reference in their entireties.

Bone cement 82 forms a cement mantle 84 over outer periphery 86 of the distal portion 90 of the body 92 of the stem 12. The cement mantel 84 has a thickness T of, for example, 0.5–24.5 millimeters.

Preferably, and is shown in FIG. 2, a cavity 94 is formed in the medullary canal 34 of the long bone 36 to permit the prosthesis 32 to be inserted therein. The cavity 94 may be formed by any of various commonly available methods for preparing the long bone 36 for the prosthesis 32.

For example, the cavity 94 made by formed by reaming and/or by broaching. The cavity 94 is formed to sufficient size to provide for the positioning of the stem 12 and for the inclusion of the cement mantel 84 between the stem 12 and the cancellous bone 96. The hard outer portion of the long bone, commonly known as cortical bone 98, is preferably not or only minimally reamed or broached to form the cavity 94.

Figure 4:
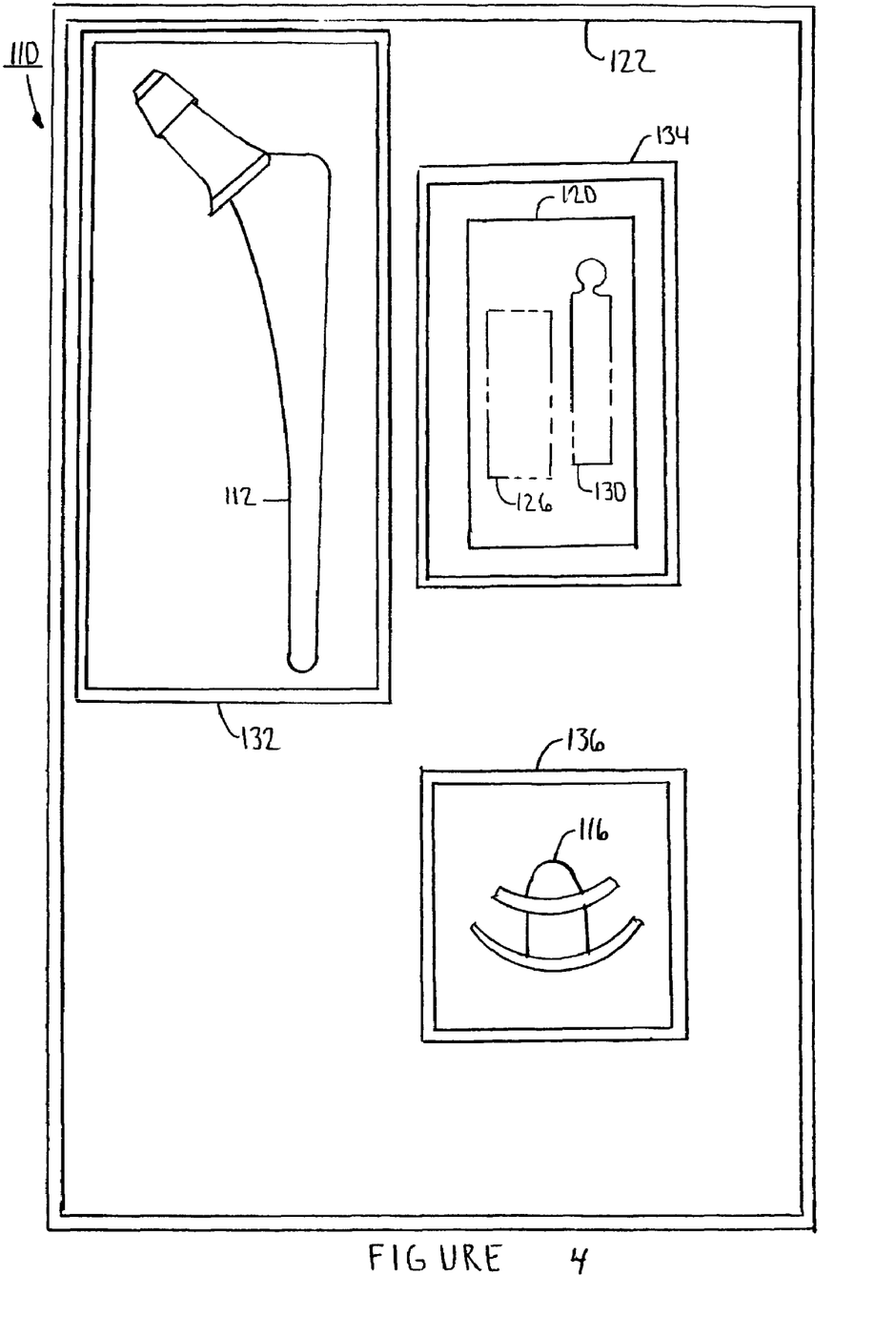
FIG. 4 is a plan view of the kit of FIG. 1 having the stem, the cement and the restrictor each individually wrapped.

Referring now to FIG. 4, according to another embodiment of the present invention, kit 110 is shown. Kit 110 is for use in implanting a stem into a long bone for use in joint arthroplasty. The kit 110 is similar to kit 10 of FIG. 1. In fact kit 110 includes a stem 112 which is similar to stem 12. It should be appreciated that while the stem 112 as shown is a femoral hip stem, the stem may be a knee femoral stem, a knee tibia stem, a humeral shoulder stem or any long bone stem. Kit 110 further includes a cement restrictor 116 which is similar to cement restrictor 16 of FIG. 1. Also kit 110 includes bone cement 120 which is similar to bone cement 20. In fact bone cement 120 includes a powder 126 similar to power 26 of the kit 10 as well as monomer 130 which is similar to monomer 30 of the kit 10.

Kit 110 unlike kit 110 of FIG. 1, includes separate packaging of the stem 110, of the bone cement 120 and of the cement restrictor 116. For example, as shown in FIG. 4, the kit 110 includes a stem container 132 for containing the stem 112. Further, the kit 110 includes a cement container 134 for containing the powder 126 and the monomer 130. Similarly the kit 110 includes a restrictor container 136 for containing the cement restrictor 116. The stem container 132, cement container 134, and restrictor container 136, are all contained within package 122 which includes the entire kit 110. The stem container 132, cement container 134, and restrictor container 136 may each be made of any suitable durable material capable of being sterilized. For example, the containers 132, 134, and 136 may be made of a metal, a paper, or a plastic. The container 132, 134, and 136 may be sterilized by any suitable sterilization method including, for example, gas plasma sterilization or gamma irradiation.

Figure 5:
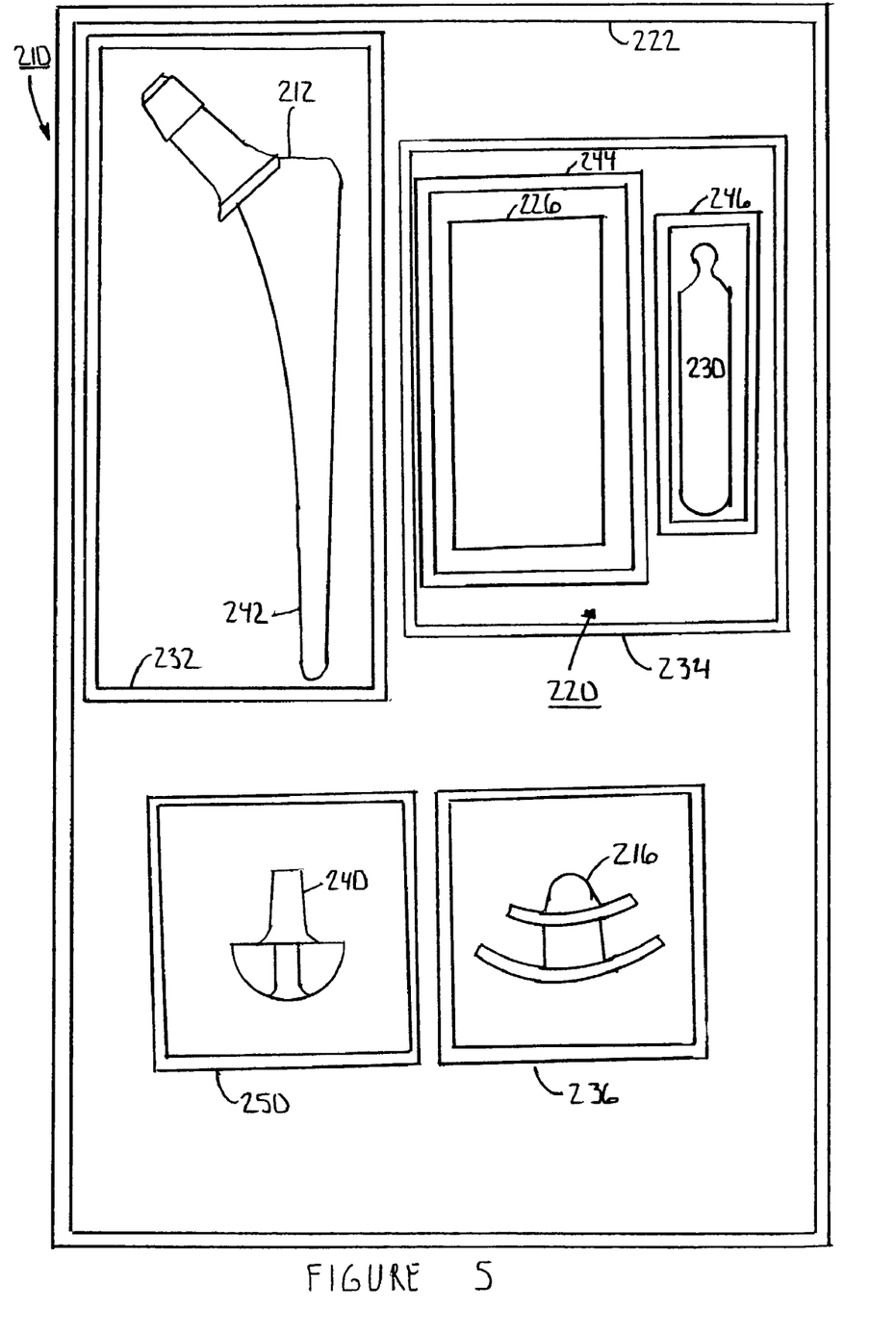
FIG. 5 is a top view of a kit for use in implanting a stem into a long bone for use in joint arthroplasty including a stem, a cement restrictor, a stem centralizer, a quantity of bone cement, and a monomer for activating the bone cement in accordance with another embodiment of the present invention.

According to another embodiment of the present invention and referring to FIG. 5, kit 210 is shown. Kit 210 is for use in implanting a stem into a long bone for use in joint arthroplasty. The kit 210 is similar to kit 110 of FIG. 4, except that kit 210 further includes a cement centralizer 240 for centralizing distal portion 242 of the stem 212 The kit 210, like the kit 110 of FIG. 4, includes a stem 212 similar to stem 112 of FIG. 1. The stem 212 is located in a stem container 232 similar to stem container 132 of FIG. 1. The kit 210 also includes bone cement 220 similar to bone cement 220 of the kit 110 of FIG. 4. The bone cement 220 includes a dry bone cement 226 similar to powder 126 of the kit 110 of FIG. 4 as well as monomer 230 similar to monomer 130 of the kit 110 of FIG. 4. The bone cement 220 is contained within a cement container 234 similar to container 134 of the kit 110 of FIG. 4.

As shown in FIG. 5, the dry bone cement 226 may be placed in a dry bone cement container 244 and the monomer 230 may be placed in a monomer container 246. The dry cement container 244 may be any suitable container for dry cement and may, for example, be made of a paper or a plastic. The container 246 for the monomer 230 may be any suitable durable material and may be, for example, a metal, plastic, or glass. Preferably, due to the volatile nature of the monomer 230, the container 246 is made of glass.

The kit 210 includes a cement restrictor 216 similar to cement restrictor 116 of the kit 110. The cement restrictor 216 is preferably positioned in a cement restrictor container 236 similar to the restrictor container 136 of the kit 110.

The stem centralizer 240 may be positioned in a stem centralizer container 250. The stem centralizer container 250 may be similar to the cement restrictor container 236 or the stem container 232 and be made of, for example, a metal, a paper or a plastic. The stem centralizer container 250 preferably is made of a material that is sterilizable by a standard sterilization techniques such as gamma irradiation or gas plasma sterilization.

The stem container 232, the cement container 234, the cement restrictor container 236 and the stem centralizer container 250 are preferably all housed in a kit container 222. The kit container 222 is similar to the kit container 122 of the kit 110 of FIG. 4.

Figure 6:
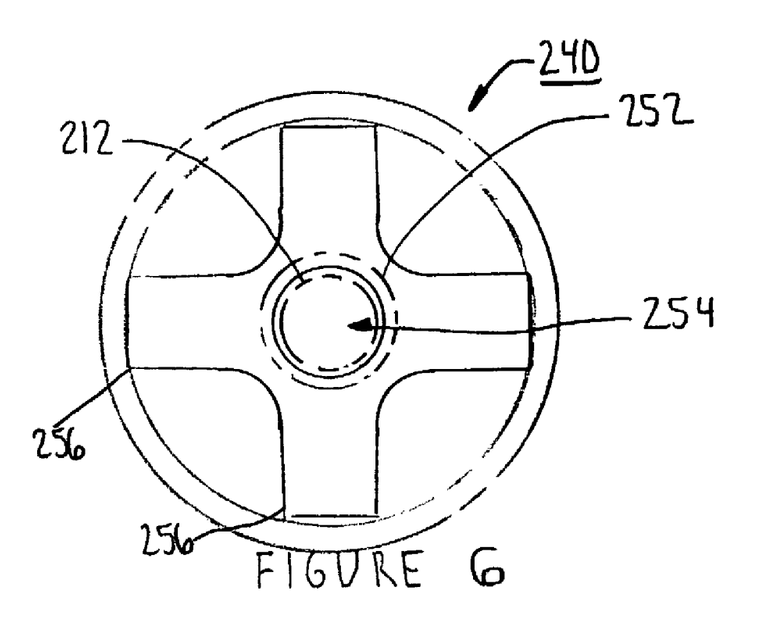
FIG. 6 is a top view of the stem centralizer of FIG. 5.
Figure 7:
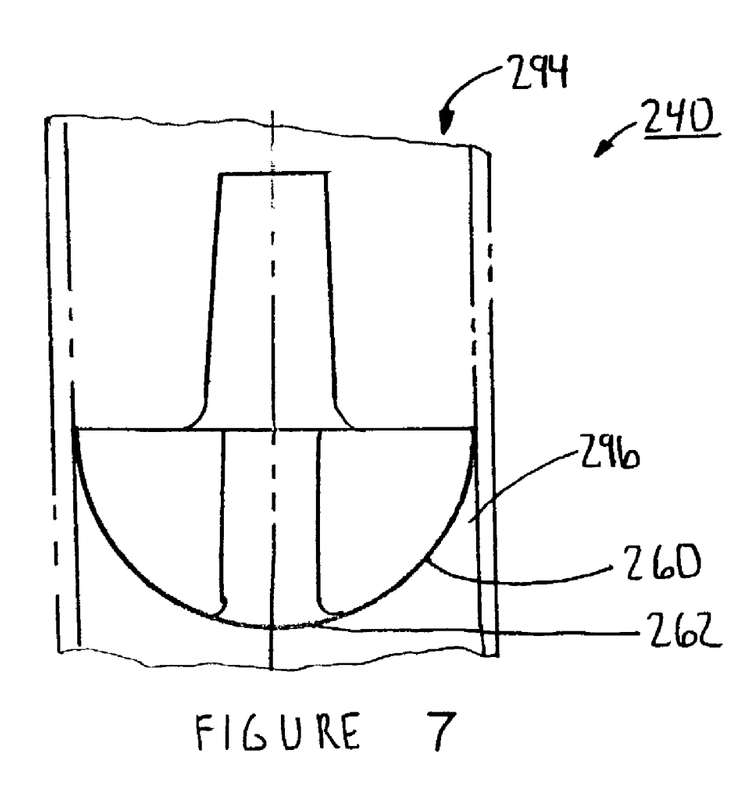
FIG. 7 is a plan view of the stem centralizer of FIG. 5.

Referring now to FIGS. 6 and 7, the stem centralizer 240 is shown in greater detail. The stem centralizer 240 may have any suitable shape capable of centralizing the stem 212 within cavity 294. Preferably the stem centralizer 240 is mattingly fitted to the stem 212 and cancellous bone 296 to accurate position the stem 212 centrally within the cavity 294. For example, and as shown in FIGS. 6 and 7, the stem centralizer 240 includes a body 252 in which defines a central through opening 254. The opening 254 is preferably adapted to slidably fit with the stem 212.

As shown in FIGS. 6 and 7, a plurality of arms 256 extend outwardly from the body 252. While as shown in FIGS. 6 and 7 four similar arms 256 are shown, it should be appreciated that as few as two or three arms made by utilized. Conversely, additional arms, in addition to the four arms shown, may be utilized in a stem centralizer 240.

As shown in FIG. 7, the arms 256 have an arcuate periphery 260 on the distal end 262 of the stem centralizer 240. The arcuate periphery 260 assists in the insertion of the stem centralizer 240 into the cavity 294.

The stem centralizer 240 may be made of any suitable durable material that is sterilizable. For example, the stem centralizer 240 may be made of a metal or a plastic. For example, the stem centralizer 240 may be made of a bone cement, for example PMMA, or of a resorbable material.

Figure 8:
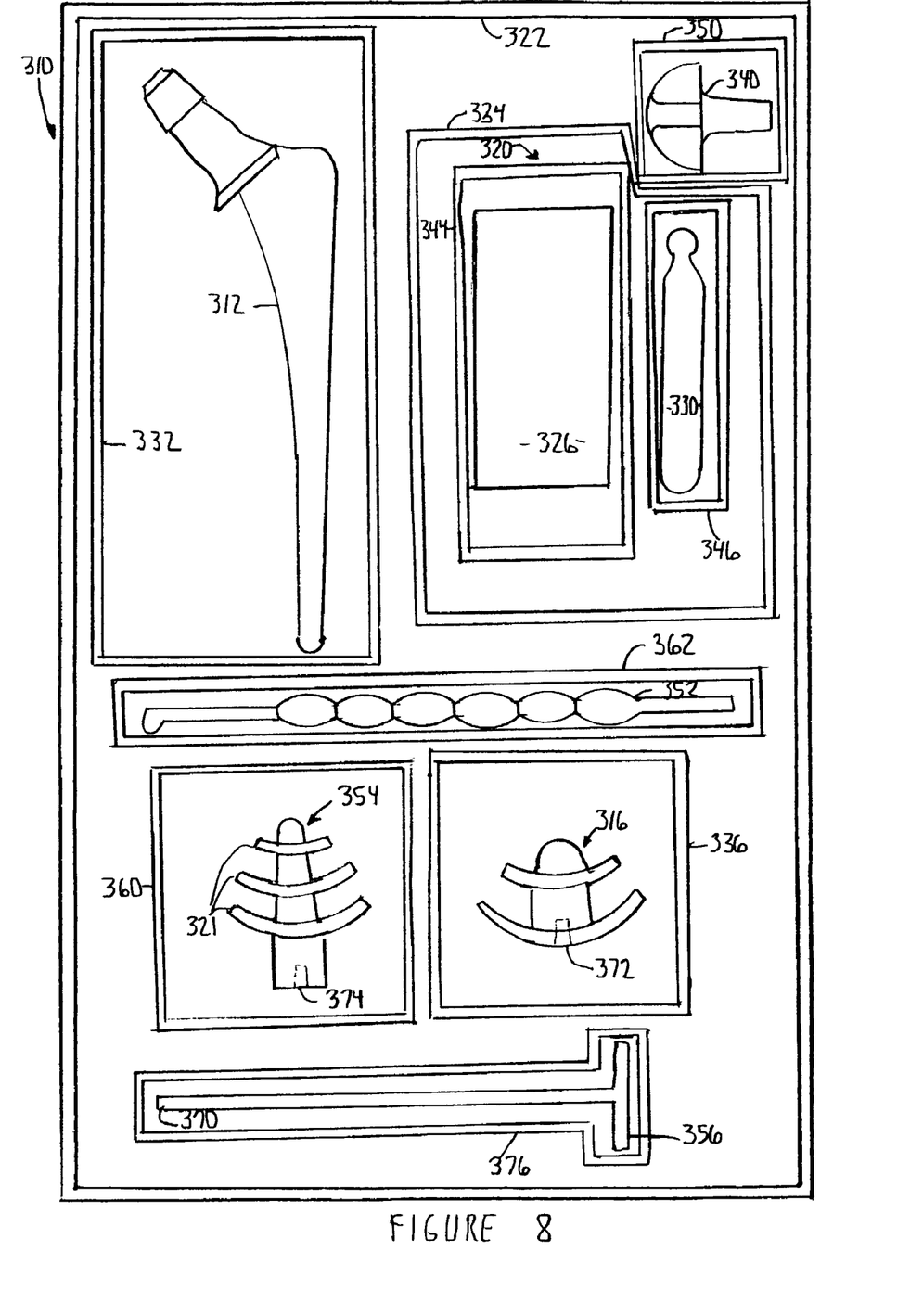
FIG. 8 is a top view of a kit for use in implanting a stem into a long bone for use in joint arthroplasty including a stem for implantation into the long bone, a first cement restrictor, a second cement restrictor, a cement restrictor inserter, a cement curette, a stem centralizer, a quantity of bone cement, and a monomer for activating the bone cement in accordance with yet another embodiment of the present invention.

Referring now to FIG. 8, an additional embodiment of the present invention is shown as kit 310. The kit 310 is for use in implanting a stem into a long bone for use in joint arthroplasty. The kit 310 is similar to kit 210 of FIG. 5, except that kit 310 further includes a curette 352, a second cement restrictor 354, and a cement restrictor inserter 356. The kit 310, like the kit 210 of FIG. 5, includes a kit container 322 similar to the kit container 222 of the kit 210.

The kit 310 includes a stem 312 similar to stem 212 of the kit 210. The stem 312 is positioned in a stem container 332 similar to stem container 232 of the kit 210. The kit 310 further includes a stem centralizer 340 similar to the stem centralizer 240 of the kit 210. The stem centralizer 340 is positioned in a stem centralizer container 350 similar to the stem centralizer container 250 of the kit 210. The kit 310 further includes a first cement restrictor 316 similar to the cement restrictor 216 of the kit 210. The first cement restrictor 316 is located in a first cement restrictor container 336 similar to the cement restrictor container 236 of the kit 210.

The second cement restrictor 354 of the kit 310 is different from the first cement restrictor 316 and may, as shown in FIG. 8, include additional fins 321 similar to the fins 21 of the cement restrictor 16 of FIG. 1. The second cement restrictor 354 may be larger or smaller in diameter from the first cement restrictor 316. The second cement restrictor 352 is to accommodate differences in the distal portion of the canal of the patient's femur. The second cement restrictor 354, like the first cement restrictor 316, is positioned in a second cement restrictor container 360 similar to the first cement restrictor container 336.

The curette 352 is included in the kit 310 to provide for additional cleaning of the bone cavity for preparation of the installation of the cement and stem 312 into the bone cavity. The curette 352 may be any standard curette which may be utilized to clean the bone cavity. For example, the curette may be a standard curette provided by DePuy Orthopaedics, Inc. The curette 352 may be packaged in a curette container 362. The curette container 362 may provide for a method of maintaining the sterilization of the curette 352. The curette container 362 may be made of any suitable material, for example, a metal, a plastic, or paper.

The kit 310 may include bone cement 320 similar to bone cement 220 of the kit 210. The bone cement 320 may include a monomer 330 as well as dry cement 326. The monomer 320 is similar to monomer 230 of the kit 210, while the dry cement 326 is similar dry cement 226 of the kit 210. The monomer 330 may be placed in a monomer container 346 similar to monomer container 246 of the kit 210. Similarly, the dry cement 326 may be placed in a dry cement container 344 similar to dry cement container 244 of the kit 210. Both the monomer 330 and the dry cement 326 may be positioned in a cement container 334 similar to the cement container 234 of the kit 210.

As shown in FIG. 8, the kit 310 may include the cement restrictor inserter 356 which is utilized to insert at least one of the first cement restrictors 316 and the second cement restrictor 360. The cement restrictor insertor 356 may have any suitable size and shape and be made of any suitable durable material capable of inserting the cement restrictors 316 and 360. For example, the cement restrictor may be made of a plastic or metal, which is sterilizable, for example, cobalt-chrome alloy steel, titanium, or stainless steel or plastic. The cement restrictor inserter may include a distal tip 370 which mattingly fits within central openings 372 and 374 in the first and second cement restrictors 316 and 360, respectively.

The cement restrictor inserter 356 may be positioned in a cement restrictor container 376. The cement restrictor container 376 may be similar to the curette container 362 and be made of a suitable durable material, for example a metal, a paper, or a plastic.

The stem container 332, the cement container 334, the stem centralizer container 350, the curette container 362, the first cement restrictor container 336, the second cement restrictor container 360 and the cement restrictor inserter container 376 may all be positioned in the kit container 322.

Figure 9:
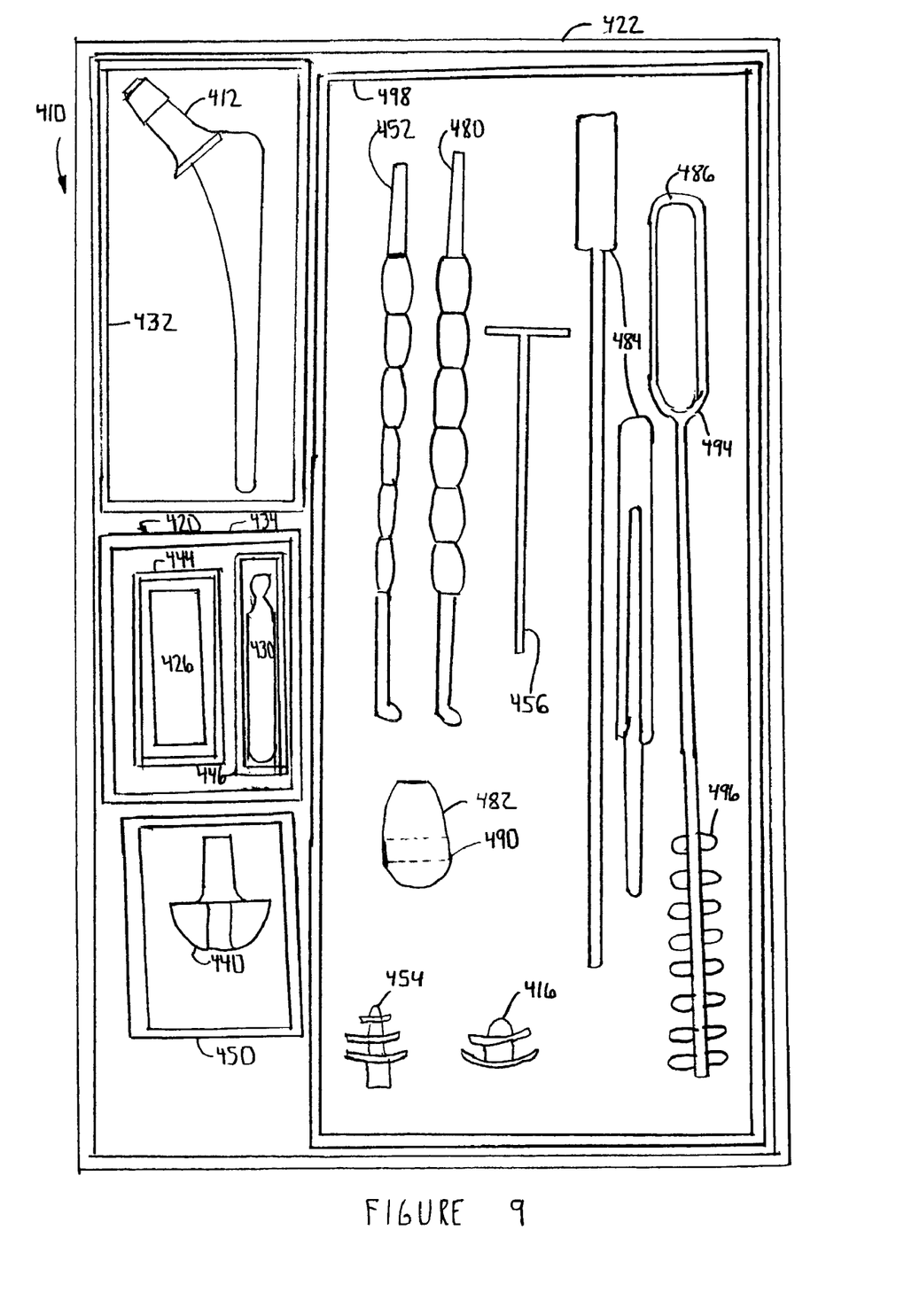
FIG. 9 is a top view of a kit for use in implanting a stem into a long bone for use in joint arthroplasty including a stem for implantation into the long bone, a first cement restrictor, a second cement restrictor, a cement restrictor inserter, two cement curettes, a stem centralizer, a femoral pressurizer, a femoral sponge, a femoral brush, a quantity of bone cement, and a monomer for activating the bone cement in accordance with yet another embodiment of the present invention.

Referring now to FIG. 9, another embodiment of the present invention is shown as kit 410. Kit 410 is for use in implanting a stem into a long bone for use in joint arthroplasty. The kit 410 of FIG. 9 is similar to the kit 310 of FIG. 8, except that the kit 410 of FIG. 9 further includes a second curette 480, a femoral pressurizer 482, a femoral sponge 484 and a femoral brush 486. The kit 410 includes a stem 412 similar to the stem 312 of the kit 310. The stem 410 is positioned in a stem container 432 similar to the stem container 332 of the kit 310.

The kit 410 further includes cement 420 similar to the cement 320 of the kit 310. The cement 420 includes a dry cement 426 similar to the dry cement 326 of the kit 310. The cement 420 further includes monomer 430 similar to the monomer 330 of the kit 310. The dry cement 426 is positioned in a dry cement container 444 similar to the dry cement container 344 of the kit 310. The monomer 430 is positioned in a monomer container 446 similar to monomer container 346 of the kit 310. The monomer 430 and the cement 426 are positioned in a cement container 434 similar to the cement container 334 of the kit 310.

The stem centralizer 440 is similar to the stem centralizer 340 of the kit 310. The stem centralizer 440 is positioned in a stem centralizer container 450 similar to the stem centralizer container 350 of the kit 310.

The kit 410 further includes a first curette 452 similar to the curette 352 of the kit 310. The kit 410 also includes a first cement restrictor 416 similar to the first cement restrictor 316 of the kit 310. The kit 410 also includes a second cement restrictor 454 similar to the second cement restrictor 354 of the kit 310. The kit 410 also includes cement restrictor inserter 456 similar to the cement restrictor inserter 356 of the kit 310.

The second curette 480 is similar to the first curette 452. The second curette 480 is either smaller or as shown in FIG. 9 larger than the first curette 452.

The femoral pressurizer 482 may be made of any suitable durable material that is sterilizable and may have any suitable shape capable of pressurizing the femoral cavity. The femoral pressurizer is positioned over the stem 412 and made, for example, include a central opening 490 for receiving the stem 412. The femoral pressurizer may be made of any suitable material and may, for example, be made of a plastic.

The femoral sponge 484 may be any sponge capable of assisting and cleaning the femoral cavity for implantation of a stem. For example, the femoral stem 484 may be a standard sponge 5402-06-000, 5402-08-000 provided by DePuy, Orthopaedics, Inc. The femoral sponge 484 may, as shown in FIG. 9, be made of two parts which may be interconnected to extend into the cavity of the stem. The femoral sponge may be made of, for example, a metal body and a synthetic sponge.

The femoral brush 486 may be made of any suitable durable material and have any particular shape. For example, the femoral brush 486 may be a standard brush 5461-22-000 sold by DePuy Orthopaedics, Inc. The femoral brush 486 may include a metal body 494 from which nylon bristles 496 extend. The body 494 and the bristles 496 may be made of any suitable durable material which is sterilizable.

The curettes 452 and 480, the restrictors 416 and 454, the femoral pressurizer 482, the insertor 456, the femoral sponges 484, and the femoral brush 486 may all be contained within a supply's container 498. The supplies container 498 may be made of any suitable durable material that is sterilizable. For example, the supply's container 498 may be made of a metal, a plastic, or paper. It should be appreciated, however, that rather than the supply's container 498, each of the first and second curettes, the first and second restrictors, the femoral pressurizer, the insertor, the femoral sponge, and the femoral brush may each individually be located in its own container.

By providing a total hip arthroplasty kit including an implant stem cement and all necessary cement products and accessories, a kit can be provided which adds additional convenience to the surgical team to reduce the amount of effort necessary to prepare for a surgery.

By providing a total hip arthroplasty kit, including a stem, cement, and cement accessories, a kit can be provided which provides additional safety in assuring that all components will be available during surgery so that either the operation may continue or that the operation continues with all necessary and helpful items.

Although the present invention and its advantages have been described in detail, it should be understood that various changes, substitutions, and alterations can be made therein without departing from the spirit and scope of the present invention as defined by the appended claims.

The invention claimed is:

1. A kit for use in implanting a stem into a long bone for use in joint arthroplasty, said kit comprising:
   a stem for implantation into the long bone;
   a cement restrictor;
   a quantity of polymethylmethacrylate powder selected to be of an appropriate quantitiy to implant the stem within the long bone;
   a plurality of inner containers, each of said plurality of inner containers for containing one of said stem, said cement restrictor and said quantity of powder; and
   an outer container for containing at least said inner container, said stem, said cement restrictor and said quantity of powder.

2. The kit of claim 1, further comprising a cement restrictor inserter.

3. The kit of claim 1, further comprising a second cement restrictor different than said first mentioned cement restrictor.

4. The kit of claim 1, further comprising a stem centralizer.

5. The kit of claim 1, further comprising a monomer for activating the powder.

6. The kit of claim 1, wherein at least two of said stem, said restrictor, and said powder are separately wrapped inside said outer container.

7. The kit of claim 1, further comprising a cement curette.

8. The kit of claim 1, wherein said quantity of powder is selected to be approximately the amount needed to implant the stem.

9. The kit of claim 1, wherein said stem, said cement restrictor, and said quantity of powder are separately wrapped inside said outer container.

10. A kit for use in implanting a stem into a long bone for use in joint arthroplasty, said kit comprising:
- a stem for implantation into the long bone;
- a cement restrictor;
- a stem centralizer;
- a quantity of polymethylmethacrylate powder selected to be of an appropriate quantitiy to implant the stem within the long bone;
- a monomer for activating the powder;
- a plurality of inner containers, each of said inner containers for containing one of said stem, said cement restrictor, said stem centralizer, said quantity of powder, and said monomer; and
- an outer container for containing at least said stem, said cement restrictor, said stem centralizer, said quantity of powder, and said monomer.

11. The kit of claim 10, further comprising a cement restrictor inserter.

12. The kit of claim 10, further comprising a second cement restrictor different than said first mentioned cement restrictor.

13. The kit of claim 10, wherein at least two of said stem, said cement restrictor, said stem centralizer, said quantity of powder, and said monomer is separately wrapped inside said outer container.

14. The kit of claim 10, further comprising a cement curette.

15. The kit of claim 10, wherein said quantity of powder is selected to be approximately the amount needed to implant the stem.

16. The kit of claim 10, wherein at least three of said stem, said cement restrictor, said stem centralizer, said quantity of powder, and said monomer are separately wrapped inside said outer a-container.

17. A kit for use in implanting a stem into a long bone for use in joint arthroplasty, said kit comprising:
- a stem for implantation into the long bone;
- a first cement restrictor;
- a second cement restrictor;
- a cement restrictor inserter;
- a cement curette;
- a stem centralizer;
- a quantity of polymethylmethacrylate powder selected to be of an appropriate quantitiy to implant the stem within the long bone;
- a monomer for activating the powder; and
- a container for containing said stem, said first cement restrictor; said second cement restrictor, said cement restrictor inserter, said cement curette, said stem centralizer, said quantity of powder and said monomer.

18. The kit of claim 17, wherein at least one of said first cement restrictor, said second cement restrictor, said cement restrictor inserter, said cement curette, said stem centralizer, said quantity of powder, and said monomer is separately wrapped inside said container.

19. The kit of claim 17, wherein all of said first cement restrictor, said second cement restrictor, said cement restrictor inserter, said cement curette, said stem centralizer, said quantity of powder, and said monomer are separately wrapped inside said container.

* * * * *